United States Patent [19]

Russack

[11] Patent Number: 5,076,423
[45] Date of Patent: Dec. 31, 1991

[54] DENTAL FLOSS DISPENSER

[76] Inventor: Anthony Russack, 144 Water St., Hackettstown, N.J. 07840

[21] Appl. No.: 611,725

[22] Filed: Nov. 13, 1990

[51] Int. Cl.⁵ .............................................. A61C 15/00
[52] U.S. Cl. .................................. 206/63.5; 132/325
[58] Field of Search .............................. 132/323-327; 206/633, 635, 210, 389, 397, 403, 408, 409, 459

[56] References Cited

U.S. PATENT DOCUMENTS

| | | | |
|---|---|---|---|
| 817,050 | 4/1906 | De La Cour | 132/325 |
| 1,454,429 | 5/1923 | Dresser | 132/325 |
| 4,019,522 | 4/1977 | Elbreder | 132/325 |
| 4,034,770 | 7/1977 | Trecker | 206/63.5 |
| 4,084,692 | 4/1978 | Bilweis | 206/63.3 |
| 4,327,755 | 5/1982 | Endelson | 206/63.5 |
| 4,606,134 | 8/1986 | Flick | 206/409 |
| 4,622,986 | 11/1986 | Harris et al. | 132/324 |
| 4,717,021 | 1/1988 | Ditzig | 206/459 |
| 4,881,560 | 11/1989 | Blank et al. | 206/63.5 |
| 4,966,319 | 10/1990 | Fleming | 206/459 |

Primary Examiner—Jimmy G. Foster
Attorney, Agent, or Firm—Thomas L. Adams

[57] ABSTRACT

A dental floss dispenser has a wallet sized case with a pair of faces and an apertured dispensing edge. A spool rotatably mounted in the case has a floss winding volume with a radial dimension many times greater than its axial dimension. Floss is spirally wound about the spool. A cutter is mounted on the outside of said case for catching and cutting the floss at the same location.

19 Claims, 3 Drawing Sheets

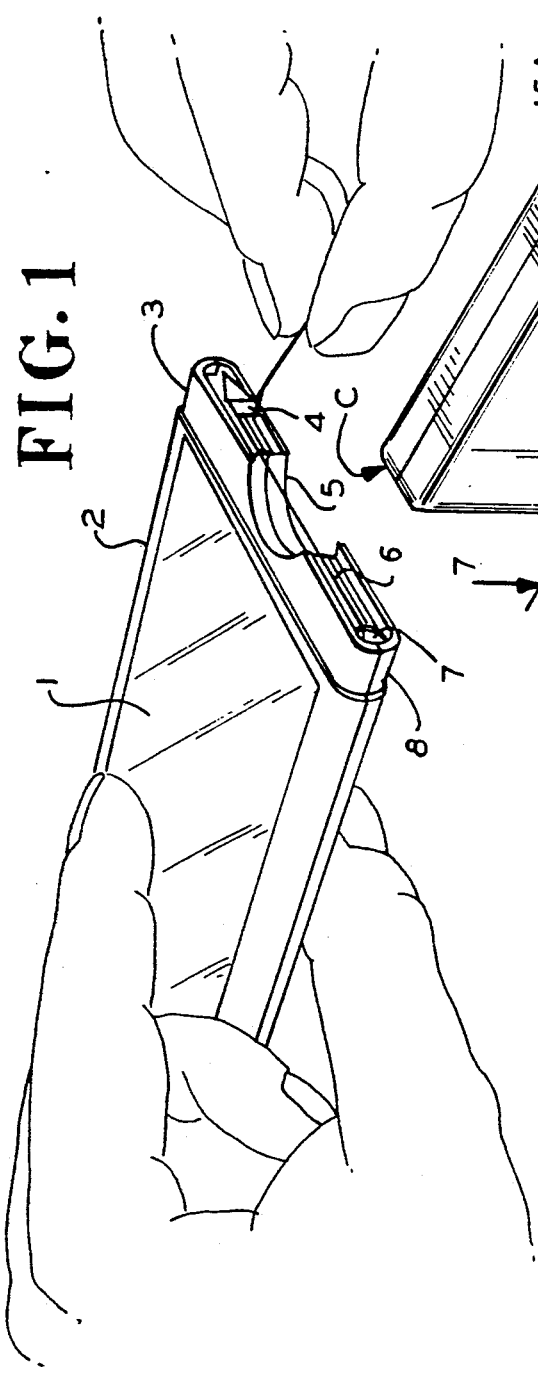
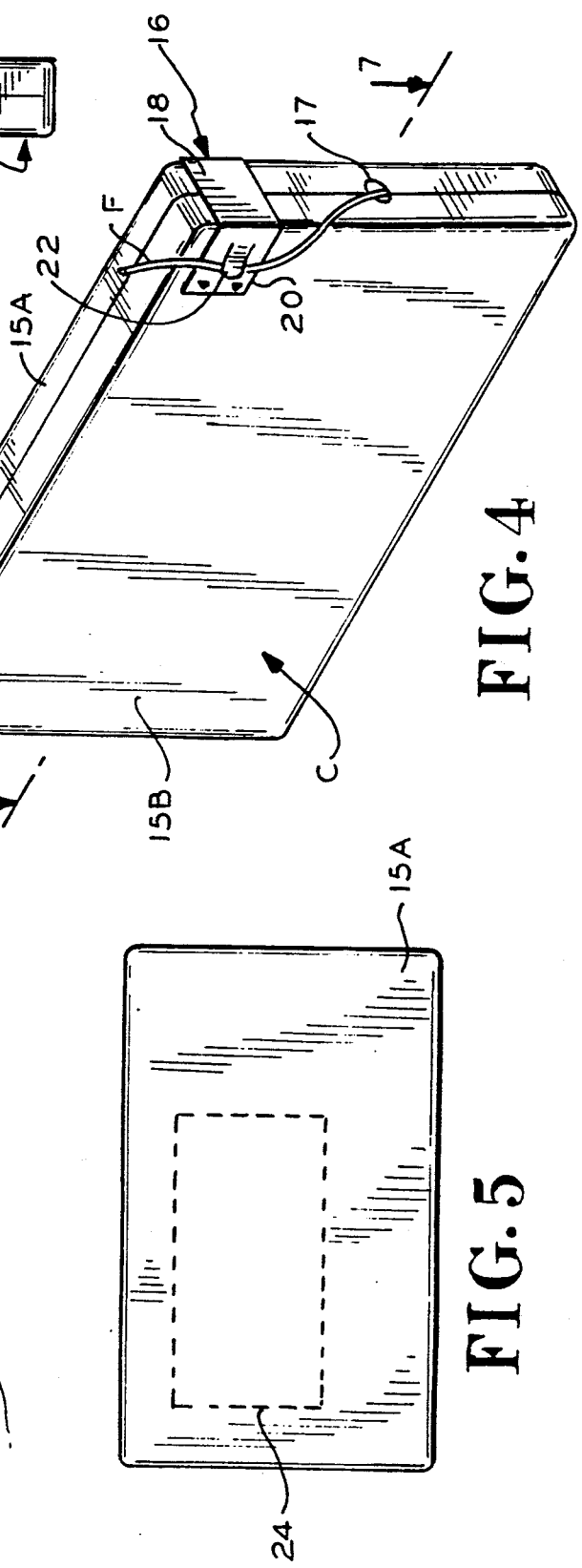
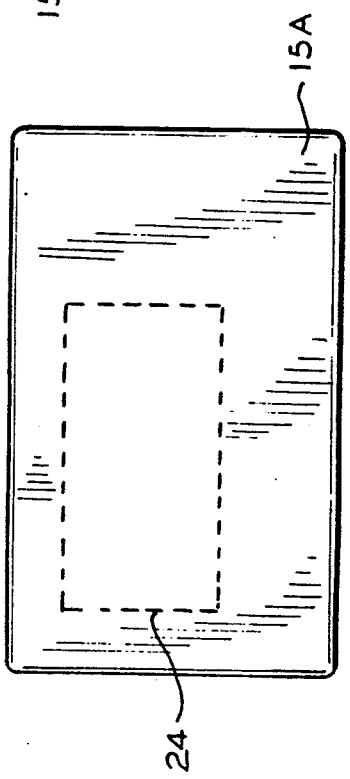

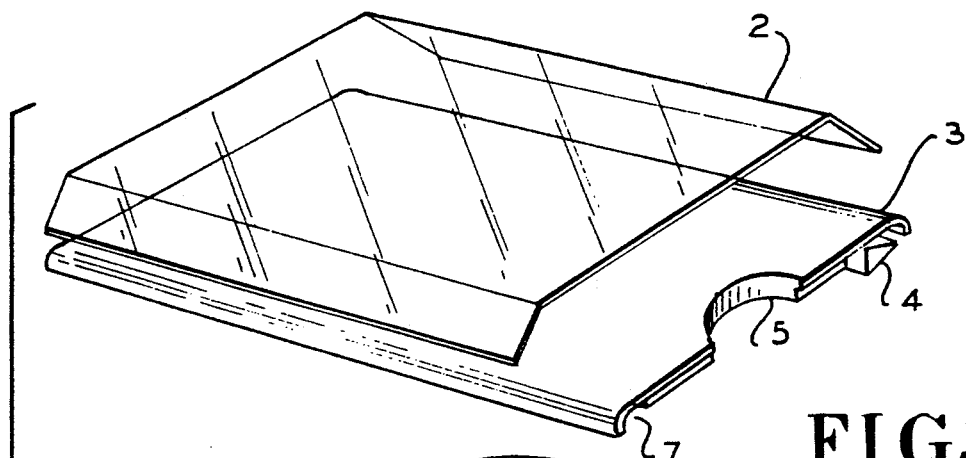
FIG. 2
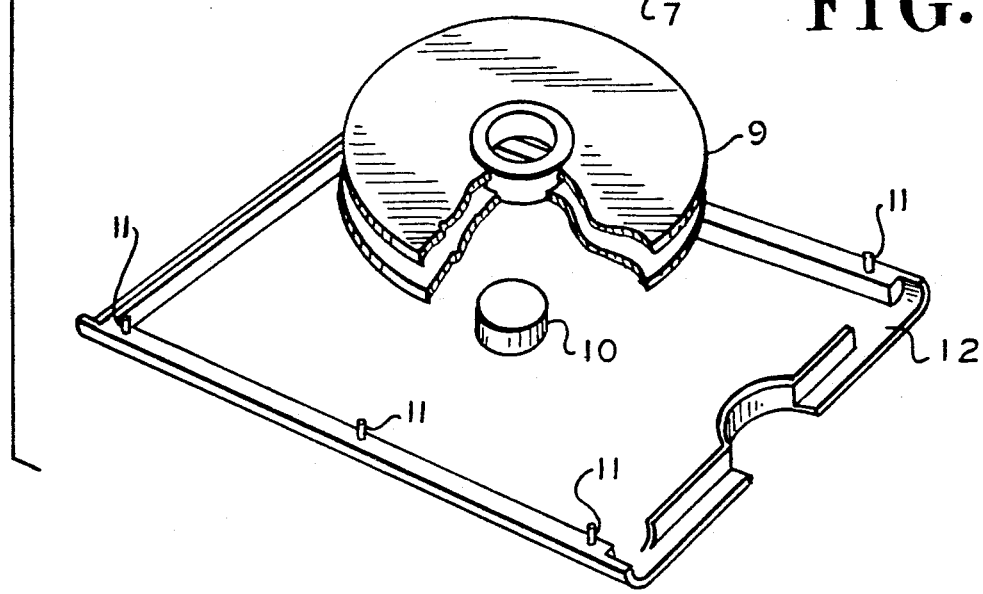
FIG. 3
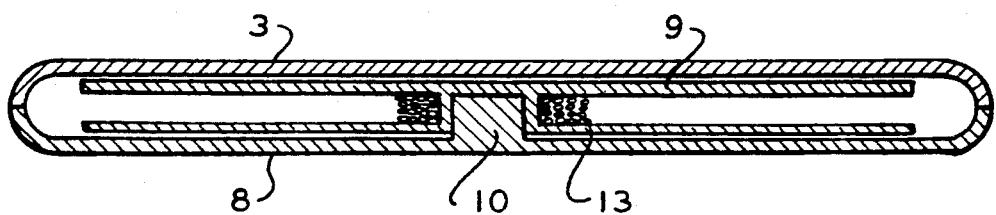
FIG. 7
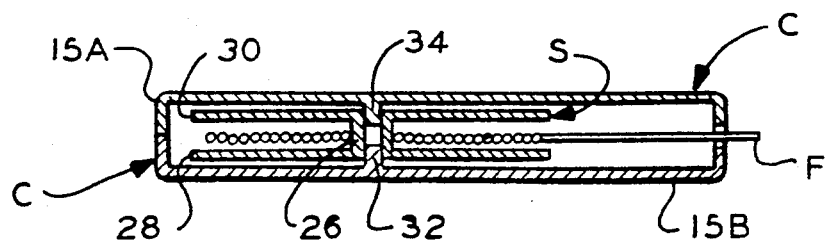

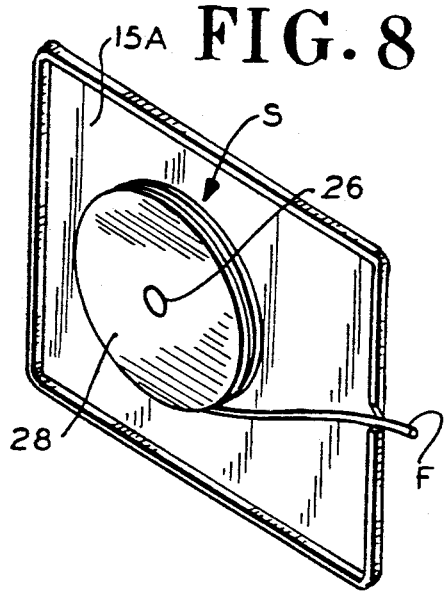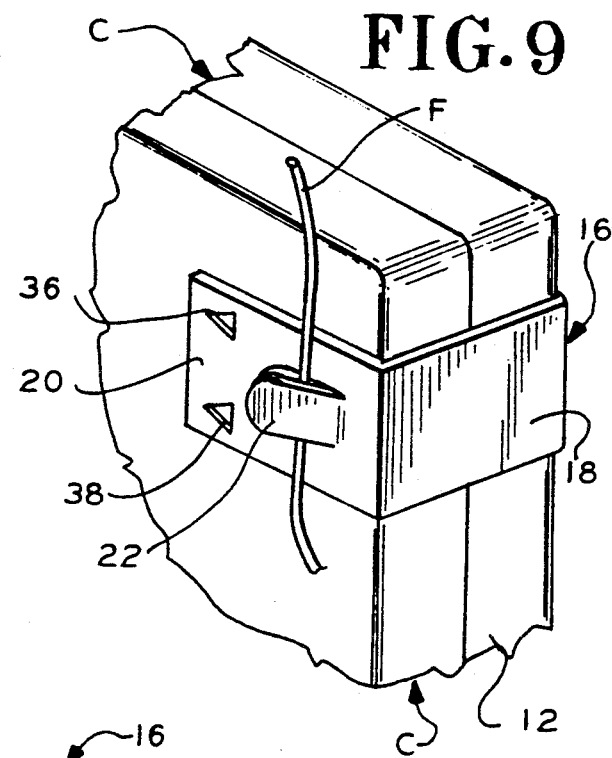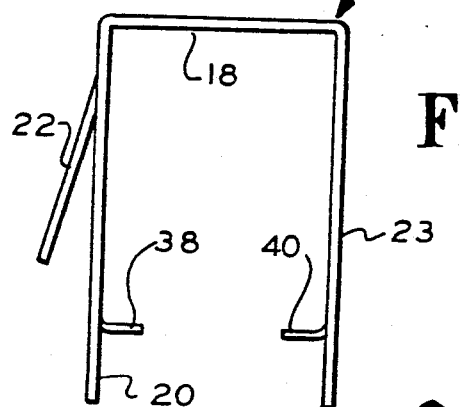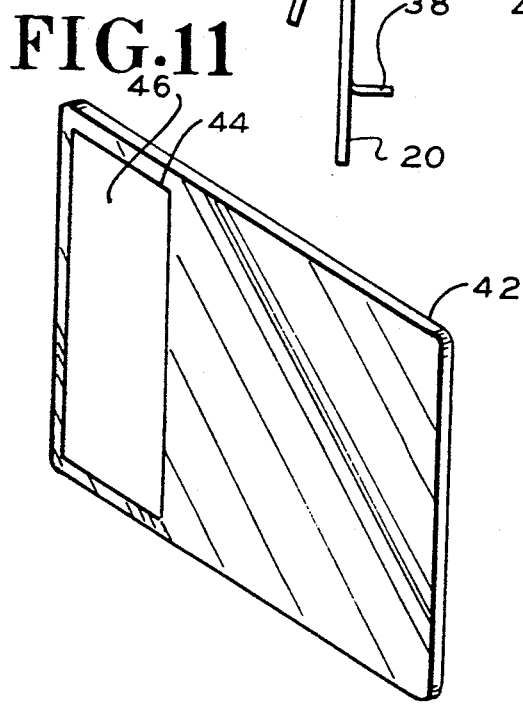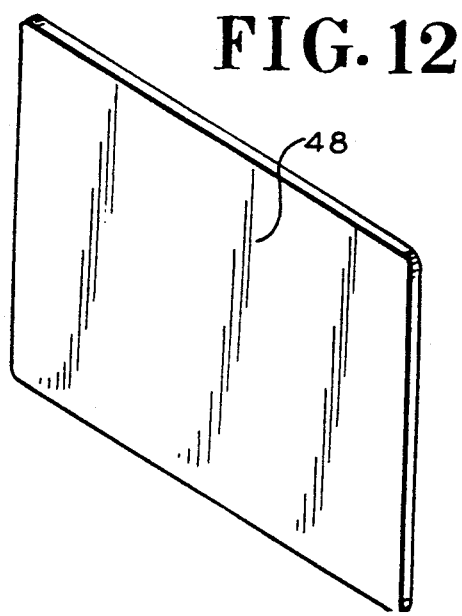

DENTAL FLOSS DISPENSER

BACKGROUND OF THE INVENTION

The present invention relates to dental floss dispensers, and in particular to a case having a spool wound with floss.

Dental professional generally agree that regular flossing promotes dental health. Consequently, people often want to floss their teeth away from home. Carrying dental floss is inconvenient when the carrying container is relatively bulky. The case in U.S. Pat. No. 3,930,059 contains a spool of floss. This case is relatively bulky and is not conveniently carried by a person.

Known floss dispensers are not easily stored in a wallet or purse. Commercially available dispensers are relatively thick and use space for features such as a hinged lid. Using a lid to protect the floss is desirable, but not when space is at a premium.

U.S. Pat. No. 4,327,755 shows a relatively thin dental floss dispenser. The floss and its cutter are exposed in this design. Consequently the floss can get dirty and become tangled when placed in a wallet or purse. Also exposing the cutter can cause unintended damage to a wallet, purse or the cutter itself. Furthermore, this dispenser uses a floss cutter at an awkward position. The cutter has a cutting blade and a spaced floss holder to allow the cutting. It would be desirable to combine the cutting and holding feature into a single unit.

In addition, this dispenser encloses a free spiral of floss. Since the floss lacks a spool, the clearance about the faces of the spiral must be kept small, otherwise the spiral will collapse. Thus without a spool the floss can easily tangle. The floss can also get wedged in a corner of the case and stop rotating. The dispenser will then either jam or floss will feed across the face of the locked spiral. This cross-wise feed twists the floss and can cause loops or knots. If the floss twists as it passes the face of the spiral, jamming is likely, even without the feared looping and knotting.

Other known floss dispensers include a floss cutter in the form of a tab partially cut and folded away from a piece of sheet metal. The tab is angled from the sheet metal to form a junction for catching and cutting the floss.

Other dispensers and holders for dental floss are shown in U.S. Pat. Nos. 1,210,205; 1,454,429; 3,804,102; and 4,657,034 as well as Design U.S. Pat. Nos. 211,880; 243,187; 245,713; 255,388 and 266,279.

Accordingly, there is a need for a floss dispenser that is compact, reliable, and easily used.

SUMMARY OF THE INVENTION

In accordance with the illustrative embodiments demonstrating features and advantages of the present invention, there is provided a dental floss dispenser including a wallet sized case having a pair of faces and a dispensing edge with an aperture therein. The dispenser has a spool rotatably mounted in the case. The spool has a floss winding volume with a radial dimension many times greater than its axial dimension. Floss is spirally wound about the spool. Also included is a cutter mounted on the outside of the case for catching and cutting the floss at the same location.

By employing a dispenser of the foregoing type, an improved arrangement is achieved. In a preferred embodiment, a relatively thin hollow case contains a spool in the form of a spindle bordered by spaced parallel disks. The floss is wound compactly about the spindle between the disks. In some embodiments an internal boss in the case acts as a shaft on which the spool can turn.

The preferred case has an aperture on one recessed edge of the case, through which the floss is pulled. A cutter is mounted on the same recessed edge of the preferred case. The recessed edge protects both the floss and cutter. The floss is kept clean and tangle-free, while the cutter neither suffers or causes damage.

In one embodiment a cutting strap wraps around the dispensing edge and is secured to opposite faces of the case. Preferably, the cutting strap has punched barbs that are embedded in the side of the case. The cutting strap has on it a deflected leaf that is angled to catch and cut the floss.

BRIEF DESCRIPTION OF THE DRAWINGS

The above brief description as well as other objects, features and advantages of the present invention will be more fully appreciated by reference to the following detailed description of presently preferred but nonetheless illustrative embodiments in accordance with the present invention when taken in conjunction with the accompanying drawings wherein:

FIG. 1 is a perspective view of a floss dispenser in accordance with the principles of the present invention;

FIG. 2 is an exploded view of the dispenser of FIG. 1;

FIG. 3 is a cross-sectional view of the dispenser of FIG. 1;

FIG. 4 is a perspective view of a floss dispenser which is an alternate to that of FIG. 1;

FIG. 5 is a rear view of the dispenser of FIG. 4;

FIG. 6 is an end view of the dispenser of FIG. 4;

FIG. 7 is a cross sectional view taken along lines 7—7 of FIG. 4;

FIG. 8 is a perspective view of the dispenser of FIG. 4 with its cutter and half of the case removed to expose the internal spool;

FIG. 9 is a detail of the cutter of FIG. 4;

FIG. 10 is a bottom view of the cutter of FIG. 4;

FIG. 11 is a perspective view of a case, which is an alternate to that of FIG. 4; and FIG. 12 is a perspective view of a case, which is an alternate to that of FIG. 11.

DETAILED DESCRIPTION OF THE PREFERRED EMBODIMENTS

FIG. 1 shows a case formed of a female housing half 3 secured to a molded male housing half 8. The case 3, 8 has a length and width approximating that of a credit card and a thickness of about the thickness of three credit cards. Case halves 3 and 8 are shown with rounded longitudinal edges and recessed front and back edges. The front edge has a floss aperture 7 through which floss 6 is pulled. The dispensing edge has a finger notch 5 in the form of a semicylindrical indentation with an axis perpendicular to the dispensing edge.

Cutter 4 is shown herein as a molded projection on case half 3. In this embodiment, cutter 4 is an "L" shaped projection having a outwardly projecting pedestal ending in a dagger that points parallel to the dispensing edge and away from floss aperture 7.

A transparent acetate shield 2 is shown in FIG. 1 wrapping at least partially around the edges of case 3. 8. As shown in FIG. 2, shield 2 is formed with edges that are folded down preparatory to attachment to case half 3. The shield 2 can either be glued or heat sealed at its edges to curl around the case 3, 8. In other embodiments, shield 2 can take the form of a sleeve that completely encircles case 3, 8. In such an embodiment, sleeve 2 can hold the case halves 3 and 8 together.

The shield 2 serves to hold and display a card 1 that can have information such as an advertisement. For example, a dental professional can display his or her name, business address and telephone number. Such a shield 2 with a card 1 makes the product especially useful for promotion.

In FIGS. 2 and 3, spool 9 is shown as a hollow spindle supporting a pair of parallel discs encompassing a winding volume. In this embodiment, the winding volume has a radial dimension many times greater than the axial dimension. Preferably, the radial dimension is an order of magnitude greater than the axial dimension, for example, a ratio of ten. Spool 9 is shown journalled on an internal boss 10 formed on the center of the inside face of case half 8.

The floss windings 13 are shown having relatively few rows, specifically, four rows. The limited number of rows results from high ratio of the radial dimension to the axial dimension. This ratio ensures that spool 9 is relatively flat and therefore allows the case 3, 8 to fit into a wallet, purse or other compact area.

In FIG. 2 case half 8 has a plurality of male connection prongs 11 that fit into corresponding female sockets (not shown) in case half 3. As shown in this view, cutter 4 projects downwardly from case 3 into the cutter space 12 in case half 8. In some embodiments, cutter 4 will be a separate metal knife mounted in slots in case 3, 8 or attached to the case by crimping, gluing or otherwise.

In operation, the floss dispenser of FIG. 1 is operated by grasping the floss 6 with fingers reaching into the notch 5. Thereafter, an appropriate length of floss 6 is pulled as spool 9 rotates (FIG. 3). When sufficient floss 6 is dispensed, the floss 6 is turned around the cutter 4 as shown in FIG. 1. The floss 6 is thus captured and then cut at the same location, that is, at cutter 4. Cutter 4 has edges which enable cutting of floss 6 in a straight forward manner.

Referring to FIGS. 4, 5, and 6, case C has complementary half shells 15A and 15B, each comprising a rectangular panel bordered by four short, perpendicular walls. Shells 15A and 15B are sized to mate together to form relatively thin, hollow case C. Floss F is shown routed through an aperture 14 centered along an edge of case C.

As illustrated, floss F is caught in a cutter shown in the form of a strap 16 having an edge panel 18 and end panel 20. Strap 16 is a "U" shaped strap straddling the edge of case C and secured on opposite faces of the case C. End panel 20 has a deflected leaf 22 angling out from end panel 20. Deflected leaf 22 is cut or punched from the base leaf forming part of end panel 20.

In FIG. 5, case half shell 15A is shown having a region 24 for receiving a label. The label can be an advertisement or can identify the name, location and telephone number of a dentist, periodontist, orthodontist or other professional distributing the dispenser.

In FIGS. 7 and 8, floss F is shown on spool S, comprising a tubular spindle 26. Spindle 26 is open at each end and encircled by a pair of spaced parallel disks 28 and 30.

In this embodiment, half shells 15A and 15B have internal bosses 32 and 34 that span shells 10 and 12 to touch end to end. In some embodiments no bosses will be used. The bosses 32 and 34 form a shaft inside spindle 26, around which spool S can turn. The bosses 32 and 34 therefore keep spool S at a defined position as it rotates.

Referring to FIGS. 9 and 10, previously mentioned cutting strap 16 has a center panel 18 bordered on opposite edges by panels 20 and 23. These two panels have the same outside dimensions. As shown herein, deflected leaf 22 is a tab having a rounded end and cantilevered from base leaf 20. Deflected leaf 22 is cut and peeled away from the center of base leaf 20. Base leaf 20 also has triangular cuts that are peeled inwardly to form barbs 36 and 38. The end panel 23 also has at complementary positions, a pair of barbs 40 arranged in the same fashion. Barbs 36, 38 and 40 are embedded into the sides of case C. In some embodiments, barbs 36, 38 and 40 can be preheated to melt and sink into the plastic of case C. In other embodiments, however, cutting strap 16 can be glued, crimped or to otherwise secured to the case.

Referring to FIG. 11, an alternate case 42 is shown with a rectangular recess 44. Recess 44 is sized to accept a label 46. The label can be an advertisement or can identify the distributor, or the distributing professional such as a dentist. Outside the label area, case 42 can have a mirror-like protective surface.

Referring to FIG. 12, an alternate case 48 is shown finished with a decorative cover. For example a fabric, plastic sheet or contact laminate can be secured to case 48.

It is to be appreciated that various modifications may be implemented with respect to the above described preferred embodiments. For example, the sizes, dimensions and proportions of the illustrated case can be altered, depending upon the size limitations and the desired floss capacity. In some embodiments the flat face of the case can be triangular, circular or have other shapes. In addition, the cutting strap can be formed of various materials and can be shaped and sized in various ways to accommodate various gauges of floss. Furthermore, the cutting junction can be placed in various positions to facilitate cutting. Also, the aperture through which floss emerges from the case can be varied and positioned at differently, depending upon the user's environment.

Obviously many modifications and variation of the present invention are possible in light of the above teachings. It is therefore to be understood that within the scope of the appended claims, the invention may be practiced otherwise than as specifically described.

I claim:
1. A dental floss dispenser comprising:
a case having a pair of faces and a dispensing edge with an aperture therein, said case being smaller than an average human adult hand;
a spool rotatably mounted in said case and having a floss winding volume with a radial dimension many times greater than its axial dimension;
floss spirally wound about said spool; and
a cutter mounted on the outside of said case for catching and cutting said floss at the same location, said cutter being a blade with an L-shape having an inner pedestal projecting away from said dispensing edge and an outer dagger pointed parallel to said dispensing edge away from said aperture, said dispensing edge along most of its length being recessed, said aperture and said cutter being located in said recess to be shielded thereby at least partially.

2. A dental floss dispenser according to claim 1 wherein said winding volume of said spool is proportioned with its radial dimension at least ten times greater than its axial dimension.

3. A dental floss dispenser according to claim 1 wherein said dispensing edge has a finger notch between said aperture and said cutter.

4. A dental floss dispenser according to claim 3 wherein said finger notch is semicylindrical and centrally located with its axis perpendicular to said dispensing edge.

5. A dental floss dispenser according to claim 4 wherein said winding volume of said spool is proportioned with its radial dimension at least ten times greater than its axial dimension.

6. A dental floss dispenser according to claim 4 wherein said case has an internal boss, and said spool comprises:
a tubular spindle and a spaced pair of parallel disks mounted on opposite ends of said spindle, said spindle being coaxially journalled about said boss.

7. A dental floss dispenser according to claim 1 further comprising:
a transparent shield mounted on one of said faces of said case with clearance for printed material.

8. A dental floss dispenser according to claim 1 wherein said floss is spirally wound in a single row about said spool.

9. A dental floss dispenser according to claim 8 wherein said spool comprises:
a spindle and a spaced pair of parallel disks mounted on opposite ends of said spindle.

10. A dental floss dispenser according to claim 9 wherein said aperture is centrally located in said edge of said case.

11. A dental floss dispenser according to claim 10 wherein said cutter comprises:
a panel partially divided to include a base leaf and a deflected leaf, said leaves being angled to catch and cut said floss at the junction of said leaves.

12. A dental floss dispenser according to claim 11 wherein said base leaf is perforated to form an opening that is shuttered from above by said deflected leaf.

13. A dental floss dispenser according to claim 10 wherein said cutter comprises:
a strap having a center panel and at right angles thereto a spaced pair of parallel end panels, one of said end panels being partially divided to include a base leaf and a deflected leaf, said leaves being angled to catch and cut said floss at the junction of said leaves.

14. A dental floss dispenser according to claim 13 wherein each of said end panels have at least one barb embedded into opposite sides of said case to attach said strap thereto.

15. A dental floss dispenser according to claim 10 wherein said case has an internal boss, and wherein said spindle is tubular and is coaxially journalled about said boss.

16. A dental floss dispenser according to claim 14 wherein said case has an external, shallow recess sized for holding labelling.

17. A dental floss dispenser comprising:
a thin, hollow case having an internal boss, an external, shallow recess sized for holding labelling, and an edge with an aperture centrally located in said edge;
a spool having a tubular spindle and a pair of parallel spaced disks mounted on opposite ends of said spindle, said spindle being coaxially journalled about said boss;
floss spirally wound in a single row about said spool; and
a cutting strap having a center panel and at right angles thereto a spaced pair of parallel end panels, one of said end panels being partially divided to include a base leaf and a deflected leaf that is angled to catch and cut said floss at the junction of said leaves, said base leaf being perforated to form an opening that is shuttered from above by said deflected leaf, each of said end panels having at least one barb embedded into opposite sides of said case to attach said strap thereto.

18. A dental floss dispenser comprising:
a case having an internal boss, a pair of faces and a dispensing edge with an aperture therein, said case being smaller than an average human adult hand;
a spool rotatably mounted in said case and a floss winding volume proportioned with its radial dimension at least ten times greater than its axial dimension, said spool having a tubular spindle coaxially journalled about said boss and a spaced pair of parallel disks mounted on opposite ends of said spindle;
floss spirally wound about said spool;
a cutter mounted on the outside of said case for catching and cutting said floss at the same location, said cutter being a blade with an L-shape having an inner pedestal projecting away from said dispensing edge and an outer dagger parallel to said dispensing edge; and
a transparent shield mounted on one of said faces of said case with clearance for printed material, said dispensing edge along most of its length being recessed to shield at least partially said aperture and said cutter, said dispensing edge having a semicylindrical finger notch centrally located with its axis perpendicular to said dispensing edge between said aperture and said cutter.

19. A dental floss dispenser comprising:
a case having a pair of faces and a dispensing edge with an aperture therein, said aperture being centrally located in said edge of said case, said case being smaller than an average human adult hand;
a spool rotatably mounted in said case and having a floss winding volume with a radial dimension many times greater than its axial dimension, said spool comprising a spindle and a spaced pair of parallel disks mounted on opposite ends of said spindle;
floss spirally wound about said spool in a single row; and
a cutter mounted on the outside of said case for catching and cutting said floss at the same location, said cutter including a strap having a center panel and at right angles thereto a spaced pair of parallel end panels, one of said end panels being partially divided to include a base leaf and a deflected leaf, said leaves being angled to catch and cut said floss at the junction of said leaves, each of said end panels having at least one barb embedded into opposite sides of said case to attach said strap thereto.

* * * * *